United States Patent [19]

Craig et al.

[11] 4,401,765

[45] Aug. 30, 1983

[54] COVALENTLY BONDED HIGH REFRACTIVE INDEX PARTICLE REAGENTS AND THEIR USE IN LIGHT SCATTERING IMMUNOASSAYS

[75] Inventors: Alan R. Craig; William A. Frey; Charles C. Leflar; Catharine E. Looney, all of Wilmington, Del.; Michael A. Luddy, West Chester, Pa.

[73] Assignee: E. I. Du Pont de Nemours and Company, Wilmington, Del.

[21] Appl. No.: 315,922

[22] Filed: Oct. 28, 1981

Related U.S. Application Data

[63] Continuation-in-part of Ser. No. 298,473, Sep. 1, 1981, abandoned.

[51] Int. Cl.³ ............................................. G01N 33/54
[52] U.S. Cl. ..................................... 436/533; 436/500; 436/805; 436/815
[58] Field of Search ................ 424/12; 23/230 B, 915; 252/408; 436/533, 805, 815, 500

[56] References Cited

U.S. PATENT DOCUMENTS

| | | | |
|---|---|---|---|
| 4,064,080 | 12/1977 | Daniel et al. | 260/8 |
| 4,166,102 | 8/1979 | Johnson | 23/230 B X |
| 4,181,636 | 1/1980 | Fischer | 260/8 |
| 4,210,723 | 7/1980 | Dorman et al. | 435/180 |
| 4,226,747 | 10/1980 | Roncari | 424/12 X |
| 4,264,766 | 4/1981 | Fischer | 536/51 |
| 4,278,651 | 7/1981 | Hales | 424/12 X |

OTHER PUBLICATIONS

H. N. Eisen, "Immunology", Harper and Row, 1974, pp. 391–394.

*Primary Examiner*—Arnold Turk

[57] ABSTRACT

Novel particle reagent for light scattering immunoassays are provided. The particle reagents are high refractive index shell-core polymers covalently bonded to compounds of biological interest. A method of measuring unknown concentrations of these compounds of biological interest by measuring changes in turbidity caused by particle agglutination or its inhibition is also provided.

15 Claims, No Drawings

COVALENTLY BONDED HIGH REFRACTIVE INDEX PARTICLE REAGENTS AND THEIR USE IN LIGHT SCATTERING IMMUNOASSAYS

CROSS REFERENCE TO RELATED APPLICATION

This application is a continuation-in-part of application Ser. No. 298,473, filed Sept. 1, 1981, now abandoned.

TECHNICAL FIELD

This invention relates to novel particle reagents consisting of shell-core particles in which the high refractive index of the core results in high sensitivity to light scattering measurements and the shell contains functional groups to which compounds of biological interest can be covalently bonded. In particular, the compounds of biological interest are antibodies or antigens and the particle reagents are designed for use in light scattering immunoassay.

BACKGROUND ART

The agglutination reaction has long been used in visual (semiquantitative) and quantitative assays for a wide variety of bacteria, cell-surface antigens, serum proteins or other analytes of clinical interest. Agglutination results from the reaction of bivalent antibodies with multivalent antigens of interest to produce aggregates which can be detected and/or measured in various ways. Similarly, the same reaction can be utilized for the detection of specific antibodies by the agglutination reaction caused by the addition of the corresponding antigen.

In order to produce large, crosslinked aggregates the number of reactive sites on the antigens must be greater than 2. Therefore, when the detection of monovalent haptens was desired, the reaction scheme was modified as follows: A multivalent form of the antigen such as a hapten-protein conjugate was prepared and the hapten present in a sample could compete with its multivalent form for the available binding sites of the antibody thereby reducing the amount of agglutination. This technique is referred to as inhibition of agglutination.

Production of multivalent forms of haptens is old in the art. Frequently the hapten is bonded to a carrier protein as is done in the preparation of immunogens. The stoichiometry of the reaction can be adjusted to place three or more haptens per protein molecule, the exact number determined by the needs of the particular assay in which the material will be utilized.

Increased sensitivity to visual or instrumental detection of agglutination or its inhibition can be achieved by the use of particle reagents as carriers, rather than soluble proteins or protein conjugates. It has been shown, for example, that antiserum to hen ovalbumin was 2000-fold more sensitive in precipitating hen ovalbumin coated on colloidion particles than in precipitating hen albumin itself; H. N. Eisen, "Immunology", Harper and Row, 1974, page 394.

Antibody particle reagents are also known. A common method for preparation of such reagents is by adsorption of the antibodies onto the surface of suitable adsorbents. Polystyrene-based latex particles have been used extensively for this purpose. These reagents, however, are susceptible to desorption during storage or use leading to variations in reagent properties. This, in turn, can adversely affect assay sensitivity and reproducibility.

To overcome the problems of desorption, particle reagents can be prepared by covalent attachment of the compounds of biological interest to the surface of particles. Polystyrene polymers have been modified to include functional groups capable of covalent protein attachment. U.S. Pat. No. 4,064,080, issued Dec. 20, 1977, discloses styrene polymers with terminal aminophenyl groups and proteins attached to them. U.S. Pat. No. 4,181,636, issued Jan. 1, 1980, discloses carboxylated latex polymers coupled to immunologically active materials through a water soluble activating agent and their use as diagnostic reagents in agglutination tests. U.S. Pat. No. 4,210,723, issued July 1, 1980, describes shell-core latex polymer particles of 0.15–1.5 $\mu$m diameter having free epoxy groups on the surface of the particles and the coupling of proteins through these epoxy groups.

Other polymeric systems have also been developed for later attachment of immunologically active materials. U.S. Pat. No. 4,264,766, issued Apr. 28, 1981, discloses latex polymers, having a particle size of 0.01–0.9 $\mu$m and having active groups such as carboxyl and amino groups to which water soluble polyhydroxy compounds can be attached covalently. Through the utilization of activating agents such as carbodiimides, immunologically active materials were attached to the latex particle/polyhydroxy compound carriers to form diagnostically useful reagents.

There is a need for a stable particle reagent which possesses high sensitivity for use in light-scattering agglutination assays and which can be prepared conveniently by the covalent attachment of compounds of biological interest to a particulate carrier.

DISCLOSURE OF THE INVENTION

The particle reagent of this invention has a high refractive index and consists essentially of:

(A) a polymer particle having an inner core and an outer shell wherein the inner core is a polymer having a refractive index of not less than 1.54 as measured at the wavelength of the sodium D line and wherein the outer shell is a polymer of (1) an ethylenically unsaturated monomer having a functional group capable of reacting with a compound of biological interest selected from the group consisting of epoxy, carboxyl, amino, hydroxyl and aldehyde, (2) optionally, other ethylenically unsaturated monomers and (3) not more than 10 parts by weight of the outer shell of the monomers of the inner core, said outer shell being formed by polymerization in the presence of said inner core; and wherein said polymer particle has an approximate diameter range of 0.03–0.1 $\mu$m and is covalently attached to (B) a compound of biological interest, its antigen or its antibody.

The compound of biological interest can be attached to the polymer particle directly or through a proteinaceous material.

A method of this invention for measuring compounds of biological interest comprises the steps of:

(A) incubating (1) a particle reagent having high refractive index consisting essentially of:

(a) a polymer particle having an inner core and an outer shell wherein the inner core is a polymer having a refractive index of not less than 1.54 as measured at the wavelength of the sodium D line and wherein the outer shell is a polymer of
  (i) an ethylenically unsaturated monomer having a functional group capable of reacting with a compound of biological interest selected from the group consisting of epoxy, carboxyl, amino, hydroxyl and aldehyde,
  (ii) optionally, other ethylenically unsaturated monomers, and
  (iii) not more than 10 parts by weight of the outer shell of the monomers of the inner core, said outer shell being formed by polymerization in the presence of said inner core and wherein said polymer particles has an approximate diameter range of 0.03–0.1 μm and is covalently attached to
(b) the compound of biological interest or its antibody;
(2) a liquid suspected of containing the compound of biological interest; and
(3) an agglutinating agent; and
(B) photometrically measuring increased particle size resulting from agglutination.

The method of this invention for measuring proteins can be carried out directly without an agglutinating agent with the appropriate complementary particle reagents.

DESCRIPTION OF THE INVENTION

This invention relates to novel particle reagents with optimal properties for use in sensitive light scattering immunoassays. The particle reagents are designed to maximize the sensitivity of the immunoassays by (1) being formed of a core material of high refractive index; (2) possessing a shell material which is capable of covalently binding to compounds of biological interest; and (3) being of a small particle size for optimal sensitivity in the immunoassays.

The light scattering properties of particle suspensions depend on several variables, most importantly the particle size, the refractive indices of the core and the suspension medium, and the wavelength of light used for measurement. Thus, the selection of core material, particle size, and wavelength of detection of the agglutination reaction are all important factors in optimizing assay sensitivity. These factors can be determined by the type of light scattering detection means used.

During visual observation of the agglutination reaction, a broad band of wavelengths, between approximately 400 and 650 nm, is being utilized. Since the light scattering response varies over this wavelength range, the visual observation results in an averaging of the effects of many wavelengths which is less sensitive than choosing the optimum wavelength for a given particle size and refractive index. For particles which are small compared to the wavelength of light, the scattering increases with the inverse 4th power of the wavelength and the magnitude is dependent upon the refractive index. When the wavelength of light approaches an absorption band of the particle, there is an increase of refractive index and thus the light scattering properties are sensitive also to the optical dispersion of the scattering element and the wavelength functionality may exceed the 4th power.

For the turbidimetric detection of particle size change at a given wavelength of measurement it is imperative that the particle size and refractive index be chosen with care since the turbidimetric signal goes through a maximum, producing a double-valued response with little or no sensitivity at the peak. In addition, the slope sensitivity is greater on the small particle size side of the peak than on the large and it increases with increasing refractive index ratio of particle to medium.

For these reasons, small particles of high refractive index with short wavelength detection are preferred for high sensitivity. There is a practical limit in the ultraviolet region for measurement of samples in serum because of light absorption by proteins and other components. Thus, convenient wavelengths are those in excess of approximately 320 nm. Longer wavelengths can be used with less sensitivity. Small particles, that is those with a diameter of less than approximately 0.1 μm, are preferred because of both increased slope sensitivity and reaction rates. For reasons of stability and synthetic convenience, particle sizes greater than approximately 0.03 μm are preferred. In general, particle size range of 0.03–0.1 μm can be utilized in the particle reagent of this invention. Shorter wavelengths, such as 340 nm, give larger signal differences than longer wavelengths, such as 400 nm.

For nephelometric detection, the optimum sensitivity can depend not only on particle size and wavelength, but also on the angle of measurement. Nephelometry refers to the measurement of the light scattered at an angle from the incident beam. The size of the particles for optimum sensitivity will have an angular dependence as well as a wavelength dependence.

Other types of scattering measurements of the agglutination reaction include particle counting, quasi-elastic light scattering, autocorrelation spectroscopy, and measurements of the dissymmetry or the polarization of the particles. These types of measurements provide different constraints for the particle reagents.

In all types of measurements, however, the higher the refractive index of the particle at the wavelength of choice, the higher the light scattering signal.

A preferred way of measurement of immunological reactions utilizing the particle reagents of this invention is by turbidity since no special equipment is required other than a spectrophotometer which is generally available in clinical laboratories. The spectrophotometer measures increased absorbance which is due to the increasing particle size resulting from the agglutination reaction. This increased absorbance is a direct measure of the agglutination caused by the analyte or an indirect measure of the agglutination inhibition caused by the analyte. To optimize the turbidity change which occurs during agglutination, it is important to select the particle size with care.

During the agglutination reaction, the effective particle size increases. For sensitive measurements it is therefore important to choose the wavelength at which the signal change for a given particle size change is optimal.

Because of the importance of the refractive index for turbidimetric detection of the agglutination reaction, core materials are restricted to those which will produce acceptable signal changes for the desired assay sensitivity. For analytes in high concentrations (μg/mL range), the choice is not critical, but for analytes in the nanogram/mL range, particles having high refractive index are necessary. Thus core polymers with high aromaticity and high atomic weight substituents are preferred over aliphatic polymers and, in general, polymers of high refractive indices are preferred over polymers with lower refractive indices.

The inner core of the polymer particles can be selected from a large group of materials with high refractive index. Preferred are those materials which can be prepared by emulsion polymerization in a manner so that the final particle size is controllable and is substantially uniform. Typical polymers utilized in the inner core of the polymer particles have refractive indices greater than 1.54 (at the Na D line, 569 nm) and are listed in Table 1. Since the refractive index is a function of wavelength, the scattering properties will be dependent upon the wavelength of measurement. In general, the refractive index is greater at shorter wavelengths.

TABLE 1

| Polymer | $n_D$ |
|---|---|
| Cellulose | 1.54 |
| Poly(vinyl chloride) | 1.54–1.55 |
| Urea-formaldehyde resin | 1.54–1.56 |
| Poly(sec-butyl α-bromoacrylate) | 1.542 |
| Poly(cyclohexyl α-bromoacrylate) | 1.542 |
| Poly(2-bromoethyl methacrylate) | 1.5426 |
| Poly(dihydroabietic acid) | 1.544 |
| Poly(abietic acid) | 1.546 |
| Poly(ethylmercaptyl methacrylate) | 1.547 |
| Poly(N—allyl methacrylamide) | 1.5476 |
| Poly(1-phenylethyl methacrylate) | 1.5487 |
| Poly(vinylfuran) | 1.55 |
| Poly(2-vinyltetrahydrofuran) | 1.55 |
| Poly(vinyl chloride) + 40% tricresyl phosphate | 1.55 |
| Epoxy resins | 1.55–1.60 |
| Poly(p-methoxybenzyl methacrylate) | 1.552 |
| Poly(isopropyl methacrylate) | 1.552 |
| Poly(p-isopropylstyrene) | 1.554 |
| Poly(chloroprene) | 1.554–1.55 |
| Poly(oxyethylene)-α-benzoate-ω-methacrylate) | 1.555 |
| Poly(p,p'-xylylenyl dimethacrylate) | 1.5559 |
| Poly(1-phenylallyl methacrylate) | 1.5573 |
| Poly(p-cyclohexylphenyl methacrylate) | 1.5575 |
| Poly(2-phenylethyl methacrylate) | 1.5592 |
| Poly(oxycarbonyloxy-1,4-phenylene-1-propyl-butylidene-1,4-phenylene) | 1.5602 |
| Poly[1-(o-chlorophenyl)ethyl methacrylate] | 1.5624 |
| Poly(styrene-co-maleic anhydride) | 1.564 |
| Poly(1-phenylcyclohexyl methacrylate) | 1.5645 |
| Poly(oxycarboxyloxy-1,4-phenylene-1,3-dimethylbutylidene-1,4-phenylene) | 1.5671 |
| Poly(methyl α-bromoacrylate) | 1.5672 |
| Poly(benzyl methacrylate) | 1.5680 |
| Poly[2-(phenylsulfonyl)ethyl methacrylate] | 1.5682 |
| Poly(m-cresyl methacrylate) | 1.5683 |
| Poly(styrene-co-acrylonitrile) (ca. 75/25) | 1.57 |
| | 1.57 |
| Poly(oxycarbonyloxy-1,4-phenyleneisobutylidene-1,4-phenylene) | 1.5702 |
| Poly(o-methoxyphenyl methacrylate) | 1.5705 |
| Poly(phenyl methacrylate) | 1.5706 |
| Poly(o-cresyl methacrylate) | 1.5707 |
| Poly(diallyl phthalate) | 1.572 |
| Poly(2,3-dibromopropyl methacrylate) | 1.5739 |
| Poly(oxycarbonyloxy-1,4-phenylene-1-methylbutylidene-1,4-phenylene) | 1.5745 |
| Poly(oxy-2,6-dimethylphenylene) | 1.575 |
| Poly(oxyethyleneoxyterephthalate) | 1.575 |
| Poly(vinyl benzoate) | 1.5775 |
| Poly(oxycarbonyloxy-1,4-phenylene-butylidene-1,4-phenylene) | 1.5792 |

TABLE 1-continued

| Polymer | $n_D$ |
|---|---|
| Poly(1,2-diphenylethyl methacrylate) | 1.5816 |
| Poly(o-chlorobenzyl methacrylate) | 1.5823 |
| Poly(oxycarbonyloxy-1,4-phenylene-sec-butylidene-1,4-phenylene) | 1.5827 |
| Poly(oxypentaerythritoloxyphthalate) | 1.584 |
| Poly(m-nitrobenzyl methacrylate) | 1.5845 |
| Poly(oxycarbonyloxy-1,4-phenylene-isopropylidene-1,4-phenylene) | 1.5850 |
| Poly(N—2-phenylethyl methacrylamide) | 1.5857 |
| Poly(4-methoxy-2-methylstyrene) | 1.5868 |
| Poly(o-methylstyrene) | 1.5874 |
| Poly(styrene) | 1.59–1.592 |
| Poly(oxycarbonyloxy-1,4-phenylene-cyclohexylidene-1,4-phenylene) | 1.5900 |
| Poly(o-methoxystyrene) | 1.5932 |
| Poly(diphenylmethyl methacrylate) | 1.5933 |
| Poly(oxycarbonyloxy-1,4-phenylene-ethylidene-1,4-phenylene) | 1.5937 |
| Poly(p-bromophenyl methacrylate) | 1.5964 |
| Poly(N—benzyl methacrylamide) | 1.5965 |
| Poly(p-methoxystyrene) | 1.5967 |
| Hard rubber (32% S) | 1.6 |
| Poly(vinylidene chloride) | 1.60–1.63 |
| Poly(sulfides) | 1.6–1.7 |
| Poly(o-chlorodiphenylmethyl methacrylate) | 1.6040 |
| Poly[oxycarbonyloxy-1,4-(2,6-dichloro)phenylene-isopropylidene-1,4-(2,6-dichloro)phenylene)] | 1.6056 |
| Poly[oxycarbonyloxybis{1,4-(3,5-dichlorophenylene)}] | 1.6056 |
| Poly(pentachlorophenyl methacrylate) | 1.608 |
| Poly(o-chlorostyrene) | 1.6098 |
| Poly(phenyl α-bromoacrylate) | 1.612 |
| Poly(p-divinylbenzene) | 1.6150 |
| Poly(N—vinylphthalimide) | 1.6200 |
| Poly(2,6-dichlorostyrene) | 1.6248 |
| Poly(β-naphthyl methacrylate) | 1.6298 |
| Poly(α-naphthyl carbinyl methacrylate) | 1.63 |
| Poly(sulfone) | 1.633 |
| Poly(2-vinylthiophene) | 1.6376 |
| Poly(α-naphthyl methacrylate) | 1.6410 |
| Poly(oxycarbonyloxy-1,4-phenylene-diphenylmethylene-1,4-phenylene) | 1.6539 |
| Poly(vinyl phenyl sulfide) | 1.6568 |
| Butylphenol-formaldehyde resin | 1.66 |
| Urea-thiourea-formaldehyde resin | 1.660 |
| Poly(vinylnaphthalene) | 1.6818 |
| Poly(vinylcarbazole) | 1.683 |
| Naphthalene-formaldehyde resin | 1.696 |
| Phenol-formaldehyde resin | 1.70 |
| Poly(pentabromophenyl methacrylate) | 1.71 |

Not all of the polymers listed above can be utilized as the inner core for the particle reagents of this invention since there are additional criteria to be applied to the selection of core monomer materials. Cellulose, for example, is not readily prepared as uniform particle size spheres. Condensation polymers are also not useful since the polymerization process does not lead to spherical particles of the type which can be obtained by emulsion polymerization. Some thermoplastic polymers such as poly(oxyethylene-oxyterephthalate) and some thermosetting resins of the urea-formaldehyde type are not suitable.

The monomers of interest are those which contain vinyl or allyl groups in addition to substituents such as halides, aromatic, heterocyclic, unsaturated or carbocyclic group which impart high refractivity.

Polymer particles useful for the preparation of the particle reagents of this invention can be prepared preferentially by emulsion polymerization. Staged emulsion polymerization can lead to a core/shell polymer approximating the desired refractive index of not less than $n_D=1.54$. To obtain a polymer of desired refractive index, it is preferred that the shell polymer not exceed approximately 10 parts by weight of the polymer particle.

A convenient way to control particle size of the polymer particles is to first prepare a seed emulsion whose size can be controlled by the amount of surfactant used. After preparation of the seed emulsion, additional monomer and surfactant can be added at a controlled rate to increase the size of the particles in the seed emulsion.

The outer shell polymer of the polymer particle can be prepared from a wide range of ethylenically unsaturated monomers having functional groups capable of reacting with compounds of biological interest. Optionally, the outer shell can also contain other ethylenically unsaturated monomers. The attachment of the shell polymer to the core can be accomplished by graft polymerization of the functional monomer to the residual ethylenically unsaturated groups in the core polymer or the functional monomer can be polymerized around the core to produce a contiguous shell. Preferred monomers include those containing an epoxy group such as glycidyl methacrylate, glycidyl acrylate, vinyl glycidyl ether, and methallyl glycidyl ether. Other functional groups include carboxyl, hydroxyl, amino, and aldehyde.

It is preferable to carry the conversion of the core monomer(s) to substantial completion so that the shell polymer be a homopolymer or a copolymer of known composition rather than a copolymer of unknown composition. Conversions in excess of 98% can be attained by increasing the temperature of the core emulsion to approximately 95° C. at the end of the polymerization. To further reduce the probability of producing particles whose surface is a copolymer of unknown composition, the shell monomer can be added gradually rather than batchwise. In such a manner, the residual core monomer(s) can be consumed during the early stages of the shell polymer formation. When the monomer utilized is one which contains an epoxy group, it is preferred that the shell polymer be a homopolymer although, as a practical matter, monomers of the inner core, up to 10 parts by weight of the outer shell, can be present.

In the case of the shell monomers containing hydroxyl, amino, aldehyde or carboxylic acid groups, care must be taken to avoid the formation of water soluble polymers. Thus, for example, acrolein or methacrylic acid cannot be utilized alone to form a homopolymer shell structure. They can be copolymerized, however, with additional monomers to produce water insoluble polymer particles.

It is also possible to modify the outer shell polymer by subsequent treatment to produce a surface capable of covalent attachment by alternative chemical techniques. For example, an epoxy group can be hydrolyzed to form a diol compound capable of reacting with cyanogen bromide which can act as a coupling agent for amine groups in proteins.

Aldehydes can react directly with amines to form a Shiff's base which can be subsequently reduced to form a covalent link. Alternatively, the aldehyde can be oxidized to an acid and carbodiimide can be used for subsequent reaction with amines to form an amide link.

The outer shell is preferably a homopolymer but can contain not more than 10 parts, preferably not more than 5 parts, and even more preferably not more than 2 parts, by weight of the outer shell of the monomers of the inner core. These monomers can be the residual monomers from the polymerization of the inner core.

The particle reagents of this invention can contain several different functional shell materials. A preferred one contains epoxy groups which can be conveniently utilized for the covalent attachment of compounds of biological interest such as haptens, antibodies, proteins or hapten-protein conjugates. Such a reaction results in the particle reagents of this invention.

The preparation of the particle reagents can be carried out as follows: The hapten or proteinaceous material, for example, can be adsorbed onto the surface of the polymer particle, followed by the reaction of the functional group, for example, the epoxide group, under suitable pH conditions, with the complementary functional group of the hapten or the proteinaceous material. Any unreacted material is then separated from the particle reagent. The conditions of the reaction are such that there should be no substantial crosslinking of particles occurring. That would result in nonuniform reagent particles and unpredictable turbidity changes during the subsequent immunoassay.

There can be two ways of preparing a particle reagent which contains a compound of biological interest covalently attached through a proteinaceous material. The compound of biological interest, such as a hapten, can first be attached to the carrier protein and then attached to the polymer particle. Alternatively, the protein can first be attached to the polymer particle and then the hapten can be attached to the protein. The second approach has the advantage of using the same protein-particle reagent for the synthesis of particle reagents having a variety of compounds of biological interest attached to them.

The surface coverage of the polymer particle by a hapten or proteinaceous material, that is the ratio of the polymer particles to compounds of biological interest, can be varied by reaction time, by dilution of the compounds of biological interest with an inactive diluent or by an additive which aids in the dispersion of the particles. While complete coverage can yield fast agglutination rates, lesser surface coverage can be important in increasing assay sensitivity.

The resulting particle reagent can be suspended in a substantially aqueous medium which can further contain buffer, serum components and surfactants to yield a monodispersed particle reagent for use in light scattering immunoassay.

The present invention is further concerned with an immunologically active, stable particle reagent for use in sensitive light scattering immunoassays for measuring compounds of biological interest. The types of assays include a wide variety of substances in biological fluids, cell and tissue extracts for which an immunological counter reactant can be produced. The compounds of biological interest include serum, plasma, salivary, urinary or milk proteins, drugs, vitamins, hormones, enzymes, antibodies, polysaccharides, bacteria, protozoa, fungi, viruses, cell and tissue antigens and other blood cell or blood fluid substances. Of special interest are those substances for which a quantitative determination is required for the assessment of disease state and various drugs.

The immunoassay can be designed in a variety of ways depending on the type of analyte and the sensitivity required.

For analytes in relatively high concentration such as certain serum proteins, appropriate antibody particle reagents can be used in a direct particle enhanced turbidimetric immunoprecipitation assay. The method of this invention provides increased detectability over conventional immunoprecipitation techniques, corresponding savings in reagent costs, and allows the use of smaller patient sample volumes. Conversely, for the detection of circulating antibodies of interest, the counter reactive antigen or antibody particle reagent can be used in a direct assay.

The inhibition immunoassay method of this invention also requires, in addition to the particle reagent, a bi- or multifunctional agent, hereinafter referred to as an agglutinating agent to cause the agglutination of the particle reagent. It is this agglutination which can be inhibited by the compound of biological interest. The agglutinating agent can be an antibody to the compound of biological interest or a particle reagent based on a polymer particle, as described above, covalently attached to an antibody of the compound of biological interest. These agglutinating agents are utilized in those situations where the particle reagent utilized in the method contains a covalently attached compound of biological interest.

The agglutinating agent can also be a multivalent conjugate of the compound of biological interest and a protein. Such a conjugate is utilized in situations where the particle reagent utilized in the method of this invention contains a covalently attached antibody of the compound of biological interest.

For the measurement of haptens, several different assay configurations can be utilized. In one such configuration, antigenic particle reagents can be prepared (either hapten-particle or hapten-protein-particle reagents) and the inhibition of the reaction of these particles with antibodies by the compound of biological interest is determined. The reaction can be performed by direct competition between the particle and the patient hapten for the antibody or by sequential reaction of the hapten with antibody followed by addition of the antigen particle reagent.

Another assay configuration for haptens utilizes antibody particle reagents wherein the agglutination of the antibody particle reagents with soluble multi-haptenic protein conjugates is inhibited by the analyte. Such an assay can also be performed in a competitive or sequential mode. In yet another assay, both antibody and antigenic particle reagents can be present, of the same or differing sizes, and the inhibition by haptens can be performed in a competitive or sequential mode.

The agglutination reaction during the method of this invention can be accelerated by the presence of an agglutinating accelerator. Such an accelerator can be a polyethylene glycol or a surfactant such as sodium dodecyl sulfate. This latter is particularly useful in an assay for digoxin utilizing a digoxin-HSA-particle reagent.

The following examples are illustrative of the invention.

EXAMPLE 1

Preparation of Polystyrene/Polyglycidyl Methacrylate Shell-Core Polymer Particle (a) A 3-liter roundbottomed flask, equipped with a stirrer and a thermostated heating mantle, is used for the polymerization which is carried out at 70° C. under a nitrogen atmosphere. The seed emulsion is prepared by adding 50 mL of styrene to 2 L of water containing 6 g of "Gafac" RE 610 (an anionic surfactant available from GAF Corp.) and 2 g of potassium persulfate. After one half of one hour, a monomer feed, consisting of 400 mL of styrene, 4 mL allyl methacrylate, and 1.5 g of Aerosol OT-100 (a dioctyl sodium sulfosuccinate, available from American Cyanamid Co.), is started at the rate of 4 mL/min. After the feed is completed, the emulsion is kept at 70° C. for one hour to insure complete conversion of the styrene. The final solids content is 15.9%, the particle size of the core polystyrene emulsion (determined by turbidity measurements at 546 nm) is 0.067 $\mu$m, and the surface tension (determined by a tensiometer using the du Nouy Ring method) is 65 dynes/cm$^2$.

(b) A 300-mL roundbottomed flask is used for the preparation of the shell-core polymer. The polymerization is carried out at 80° C. under a nitrogen atmosphere. 200 mL of the core polystyrene emulsion (Example 1a) is added to 50 mL of water containing 0.2 g of potassium persulfate and 0.2 g of anhydrous potassium carbonate, followed by the addition of 3.9 mL of glycidyl methacrylate at a rate of 0.1 mL/min. After 45 min the mixture is cooled. The final shell-core polymer has a particle size of 0.069 $\mu$m.

EXAMPLE 2

Preparation of Polystyrene/Polyglycidyl Methacrylate Shell-Core Polymer Particle (a) A 3-liter roundbottomed flask, equipped with a stirrer and a thermostated heating mantle, is used for the polymerization. Styrene is purified prior to polymerization by passing through a column packed with basic alumina. The polymerization is performed at 70° C. under a slow stream of nitrogen.

The polymerization is started by adding 45 mL of styrene, 5 mL of ethylene glycol dimethacrylate, 50 mL of a 30% solution of sodium dodecyl sulfate in water, and 2 g of potassium persulfate to 2 L of deionized water. This mixture is allowed to polymerize at 70° C. for 20 min. At this point, the particle size is 0.021 $\mu$m and the surface tension is 38.8 dynes/cm$^2$, indicating that substantially all of the surfactant is utilized for particle stabilization.

The particles are then grown to a final size of 0.043 $\mu$m by gradually adding 400 mL of styrene and 10 g of "Aerosol" OT-100 at a rate of 4 mL/min. The final size is predicted to be 0.044 $\mu$m, based on the initial particle size and the volume of added styrene.

590 mL of seed emulsion, prepared above, is added to 1510 mL of deionized water containing 1.5 g of potassium persulfate and is heated to 70° C. When the mixture reaches 70° C., 340 mL of styrene and 3.4 g of "Aerosol" OT-100 are added at a rate of 4 mL/min. When the feed is complete, the temperature is increased to 95° C. for 0.5 h to insure high conversion of the monomers. The conversion is 98.4% complete, as measured by gas chromatography of an ether extract of the emulsion. The final core size is 0.070 $\mu$m. (The predicted value is 0.069 $\mu$m, calculated from the initial size and the volume of styrene added.)

(b) 200 mL of water, containing 2 g of potassium carbonate and 2 g of potassium persulfate, is added to the core polymer prepared in (a) above and the reaction temperature is adjusted to 80° C. 50 mL of glycidyl methacrylate is then added at a rate of 1.5 mL/min. A total of 45 min is allowed for the shell polymerization. The final particle size is 0.71 $\mu$m and the glycidyl methacrylate conversion is 97.3% (using a gas chromatographic measurement as with the styrene). The final styrene conversion appears to be complete since no styrene is detectable by chromatography.

EXAMPLE 3

Preparation of Polyvinyl Carbazole/Polyglycidyl Methacrylate Shell-Core Polymer Particle A 300-mL roundbottomed flask, equipped with a distillation head and a mechanical stirrer, is utilized. 200 mL of water containing 0.5 g of potassium persulfate, 0.5 g of trisodium phosphate dodecahydrate, and 1.5 g of sodium dodecyl sulfate are heated to 70° C. under a nitrogen atmosphere. A seed emulsion is formed by adding 4.5 mL of styrene and 0.5 mL of ethylene glycol dimethacrylate. After 30 min the seed emulsion has a particle size of 0.021 $\mu$m and pH of 8.5. A solution of 20 g of vinyl carbazole and one gram of "Aerosol" OT-100 in 10 mL of dichloromethane is then added at a rate of 0.1 mL/min. The dichloromethane is removed by distillation as soon as it is added. After the core emulsion is complete, 0.1 g of potassium persulfate in 10 mL of water is added, and then 2.5 mL of glycidyl methacrylate is added at a feed rate of 0.1 mL/min. 45 min is allowed for the polymerization. The final particle size is 0.041 $\mu$m. The final solids content is 10.5%.

EXAMPLE 4

Preparation of Polystyrene/Polyglycidyl Methacrylate Shell-Core Polymer Particle (a) The procedure of Example 1(a) is utilized as follows. To 2 L of water containing 2 g of azobisisobutyramidine hydrochloride are added 50 mL of styrene and 2 g of cetyl trimethyl ammonium bromide and allowed to polymerize for 30 min. Then, a mixture of 200 mL of styrene and 2 mL of allyl methacrylate is added at a rate of 4 mL/min. After the addition of 100 mL, and again at the completion of the addition, 0.75 g of cetyl trimethyl ammonium bromide is added. The final solids content is 10.5% and the particle size is 0.106 $\mu$m.

(b) A mixture of 200 mL of the core emulsion prepared in Example 4(a) above, 0.2 g of azobisisobutyramidine hydrochloride, and 0.2 g of sodium acetate (anhydrous) dissolved in 10 mL of water is heated to 70° C. under a nitrogen atmosphere. After the temperature is stabilized, 3 mL of glycidyl methacrylate is added at a rate of 0.1 mL/min. 45 min is allowed for the polymerization. The final emulsion has a surface tension of 48.5 dynes/cm$^2$.

EXAMPLE 5

Preparation of Gentamicin Particle Reagent and its Use 50 mg of gentamicin sulfate in 5 mL of water is neutralized by adding barium hydroxide until no further precipitate is formed. The precipitate, barium sulfate, is removed by centrifugation. The supernatant is added to a mixture of 5 mL of the polystyrene/polyglycidyl methacrylate polymer particle prepared in Example 4 and 5 mL of a 0.1% suspension of "Schercozoline" S (a substituted imidazoline from stearic acid, available from Scher Chemical Co.) at a pH of 8.5 adjusted with potassium hydroxide. The mixture is warmed to 75° C. for approximately 30 min, diluted with 200 mL of water, and deionized using a mixed bed ion exchange resin. 0.4 mL of the resulting particle reagent is added to 20 mL of 0.1% sodium dodecyl sulfate (SDS) followed by the addition of 0.2 mL of 0.020 M phosphate buffer (pH 7.43) containing 0.3 m NaCl and 0.1% SDS.

1.5 mL of this mixture is tested for immunological reactivity by adding, separately, human serum, gentamicin, anti-gentamicin (rabbit antiserum, Kallestad Laboratories, Inc.), and a mixture of anti-gentamicin and gentamicin and by measuring the turbidity. The results, expressed in Table 2 as the rate of change in turbidity, indicate that the particle reagent is immunologically active and can be used for the measurement of gentamicin.

TABLE 2

| Inhibition of Turbidimetric Activity by Gentamicin | |
|---|---|
| Sample | Rate (mA/min at 340 nm) |
| 15 $\mu$l human serum | 1 |
| 0.2 $\mu$g gentamicin | 2 |
| 15 $\mu$l anti-gentamicin | 74 |
| 15 $\mu$l anti-gentamicin and 0.2 $\mu$g gentamicin | 66 |

EXAMPLE 6

Measurement of Theophylline (a) Preparation Of 8-(3-Carboxypropyl)-1,3-Dimethylxanthine The 8-substituted theophylline derivative, 8-(3-carboxypropyl)-1,3-dimethylxanthine, is synthesized according to the previously published procedure of C. E. Cook, et al., Res. Commun. in Chemical Pathology and Pharmacology, Vol. 13, 497–505 (1976) as follows: Glutaric anhydride (6.8 g) and 4,5-diamino-1,3-dimethyl pyrimidine-2,6-dione (6.2 g) are refluxed under nitrogen in 15 mL of N,N-dimethylaniline for 3 h using a Dean-Stark trap. The mixture is cooled, filtered, and the solid product (3.6 g) is recrystallized twice from water. The purified derivative has a melting point of 254°–255° C. and the expected parent ion peak in the mass spectrograph of m/e=266.

(b) Attachment of a Theophylline Derivative to Polymer Particles

The 8-substituted theophylline derivative prepared in part (a) above is attached directly to the polystyrene/polyglycidyl methacrylate polymer particles prepared in Example 1 as follows: 8-(3-carboxypropyl)-1,3-dimethylxanthine (50 mg) and 0.6 mL of the latex (17% solids) are heated in 0.015 M sodium phosphate buffer (pH 7.3, 50 mL) for 1 h. The pH of the mixture is adjusted to 5.4 and heated for an additional 1 h. The pH is then adjusted to 2.3 and heated for a final 1 h. The mixture is then centrifuged (80 min, at a force of 40,000×g), resuspended in an equal volume of 0.1% sodium dodecyl sulfate, recentrifuged, and suspended again in 0.015 M sodium phosphate (pH 7.8) containing 0.1% polyethylene glycol (PEG) 6000. The reagent is then dialyzed against the same buffer.

(c) Measurement of Theophylline

This measurement is performed at 37° C. on the 'aca' instrument. 0.020 mL of sample containing an unknown amount of theophylline is added to 4.98 mL of 0.15 M phosphate buffer, pH 7.8, containing 2.5% (w/v) PEG 6000. 0.004 mL of rabbit anti-theophylline antiserum (Kallestad Laboratories, Inc.) is added and the reaction is initiated after a 3.5-min incubation period by the addition of 0.150 mL of the particle reagent prepared in part (b) above, containing 3% solids. The increase in turbidity due to particle aggregation is measured as the difference in the absorbance at 340 nm (rate of change) 29 s and 46 s after particle addition. Table 3 shows the data for a standard curve for the assay of serum theophylline; the results obtained with the unknown sample are compared to this curve to provide the amount of theophylline present. (Theophylline standards are prepared by appropriately diluting with human serum a solution of known concentration of theophylline in water. The assay results from the standards provide the data for the standard curve.)

TABLE 3

Inhibition of Turbidimetric Activity by Serum Theophylline

| Theophylline Concentration (µg/mL) | Rate (mA/min at 340/mm |
|---|---|
| 0 | 192 |
| 0.5 | 170 |
| 1.0 | 149 |
| 3.3 | 114 |
| 5.0 | 106 |
| 20.0 | 55 |
| 40.0 | 32 |

EXAMPLE 7

Attachment of Human Serum Albumin to a Polymer Particle (A procedure similar to what is described here can be used for the attachment of IgG, various drugs and drug conjugates such as digoxin-HSA, theophylline-HSA, gentamicin-HSA, tobramycin-HSA and thyroxine-catalase conjugates to the polymer particles).

To 1.2 L of a solution (0.3 M NaCl, 0.02 M phosphate, pH 9.7) containing 1 mg/mL HSA, is added dropwise, with stirring and sonication, 6 mL of the latex polymer particles (10% w/v) prepared in Example 1. The suspension is stirred, sonicated, and heated (50° C. for 1 h). The suspension is then centrifuged for 7 h at 12,500 rpm using a Du Pont Sorvall ® Model RC-5B centrifuge and a GSA rotor to remove any unbound HSA. The particle pellet is resuspended in 500 mL of 0.1% sodium dodecyl sulfate (SDS) in the above buffer, heated to 50° for 1 h and centrifuged again using the same conditions. The particle pellet is resuspended again in 250 mL of 0.1% SDS, sonicated and centrifuged for 2 h at 19,500 rpm using an SS 34 rotor. The particle pellet is resuspended in 60 mL of 0.1 M glycine buffer, pH 7.6 containing 0.15 M NaCl (GBS buffer) containing 0.1% HSA and then centrifuged for 80 min at 19,500 rpm using a SM24 rotor. The particle pellet is finally resuspended in 60 mL of the glycine buffered saline/HSA solution to yield a 1% (w/v) suspension of the particle reagent with a protein bonded to its surface for possible later covalent attachment of compounds of biological interest. It is stored at 4° C.

EXAMPLE 8

Measurement of Bovine Serum Albumin (a) Attachment of BSA to Polymer Particles

A 2.0 mg/mL bovine serum albumin (BSA) solution is prepared by dissolving 20 mg BSA (Sigma Chemical Co., Fraction V) in 10 mL of 0.3 M NaCl with 20 mM sodium phosphate, pH 9.7. A 0.060 mL aliquot of the latex polymer particles (Example 1) (14% w/v suspension, 0.069 µm diameter) is then added to the BSA solution and sonicated for 1 h at 50° C. Conditions for subsequent centrifugation and sonication are as given in Example 7 with appropriate reduction in the volumes used.

(b) Assay for BSA

Assays are conducted in a Cary 219 spectrophotometer at 37° C. using 3.0-mL cuvettes containing 2.0 mL buffer (0.15 M sodium phosphate, pH 7.8 with 4.5% (w/v) polyethylene glycol 6000, PEG). 0.050 mL of a sample containing different levels of BSA and 0.050 mL of the antiserum (Miles Biochemicals, anti-BSA, undiluted) are added to the cuvette and allowed to incubate for 5 minutes before 0.050 mL of the BSA-coated particles are included. Upon adding the BSA-particle reagent prepared in (a) above, the extent of aggregation is monitored by following the change in absorbance at 340 nm. Table 4 shows that the rates of aggregation can be inhibited by increasing levels of BSA in the samples.

TABLE 4

| Inhibition of Turbidimetric Activity by Sample BSA | |
|---|---|
| BSA Concentration (mg/mL) in Sample | Rate (mA/min at 340 nm) |
| 0 | 350 |
| 1 | 300 |
| 2 | 240 |
| 10 | 36 |

EXAMPLE 9

Measurement of Haptoglobin (a) Attachment of Haptoglobin to Polymer Particles

A 0.030-mL portion of a polystyrene/polyglycidyl methacrylate polymer particle latex (17% w/v suspension, 0.076 µm diameter, prepared in a manner similar to Example 1) is added to 5 mL of a solution containing 1.0 mg/mL human haptoglobin (Calbiochem-Behring Corp.) in 20 mM sodium phosphate, pH 9.7. After sonicating for 1 h at 50° C. in a Branson ® model B-22-4 water bath sonicator, the suspension is centrifuged at 19,000 rpm in a Du Pont Sorvall ® model RC-5B centrifuge. The pellet of particles resulting after two hours is resuspended in 5 mL of 0.1% (w/v) sodium dodecyl sulfate. The pellet resulting after a further 40 min of centrifugation is resuspended in 5 mL of 0.2 M glycine, pH 7.4 and centrifuged again. To completely disperse the particles, the final pellet is resuspended in 1 mL of 0.2 M glycine by sonicating for 5 minutes with a Heat Systems Ultrasonics ® model W-185-F sonicator.

(b) Assay for Haptoglobin

Assays are performed on a Carey 219 spectrophotometer at 37° C. with 3.0 mL quartz cuvettes containing 2.0 mL of 0.150 M sodium phosphate buffer, pH 7.8. 0.050 mL of anti-human haptoglobin antiserum (Calbiochem-Behring Corp.) is incubated for 3 minutes at 37° C. with 0.040 mL of sample which contains free haptoglobin in the aforementioned buffer. After the incubation period, 0.050 mL of the haptoglobin-particle reagent prepared in (a) above (0.10% w/v particle) is added and the initial rate of absorbance change at 340 nm is monitored. Table 5 shows the measured rate as a function of haptoglobin concentration.

TABLE 5

Inhibition of Turbidimetric Activity by Sample Haptoglobin

| Haptoglobin Concentration (mg/mL) | Rate (mA/min at 340 nm) |
|---|---|
| 0 | 218 |
| 0.1 | 125 |
| 0.2 | 75 |

TABLE 5-continued

Inhibition of Turbidimetric Activity by Sample Haptoglobin

| Haptoglobin Concentration (mg/mL) | Rate (mA/min at 340 nm) |
|---|---|
| 0.4 | 28 |
| 1.0 | 0 |

EXAMPLE 10

Measurement of Gentamicin (a) Attachment of Gentamicin-Human Serum Albumin Conjugate to Polymer Particles To a solution of 1.5 g of gentamicin sulfate (Sigma Chemical Co.) and 1.5 g of human serum albumin (globulin free, Sigma Chemical Co.) in 50 mL of distilled water is added 6.25 g of N-ethyl-N'-(3-dimethylaminopropyl) carbodiimide hydrochloride with stirring. The pH of the solution is adjusted to 6.0 by the addition of 0.1 N hydrochloric acid. The mixture is kept at room temperature for 18 h and then dialyzed against 15 mM sodium phosphate buffer (pH 7.8) at 4° C.

The gentamicin-HSA conjugate is then carboxymethylated to prevent nonspecific precipitation of the particles. The buffered conjugate prepared above is diluted to obtain 500 mL of a solution containing 6 M guanidine hydrochloride and 0.1 M tris(hydroxymethyl)aminomethane, pH 8.2. 2.5 mL β-mercaptoethanol is added slowly with stirring. The mixture is kept at 37° C. for 2 h followed by the addition of 12.5 g iodoacetic acid, sodium salt, slowly with stirring. The pH is readjusted to 8.2 with the addition of 1 N sodium hydroxide. After 2 h at 37° C., the product is dialyzed against 0.30 M sodium chloride and 20 mM phosphate buffer, pH 7.8. Any precipitated protein can be removed by centrifugation at 12,500 rpm for 20 min.

The preparation of the gentamicin-HSA-particle reagent, using the gentamicin-HSA conjugate, is carried out according to the procedure given in Example 7.

(b) Assay for Gentamicin

The assay is performed at 37° C. on the 'aca' instrument. 0.010 mL of sample containing gentamicin is added to 4.99 mL 0.15 M phosphate buffer, pH 7.8, containing 2.5% (w/v) polyethylene glycol (PEG) 6000. 0.015 mL of the antiserum (Kallestad Laboratories, Inc.) anti-gentamicin-BSA from rabbit, 1/250 to 1/500 final dilution) is added. After 3.5 min incubation at 37° C., the reaction is initiated with the addition of 0.050 mL of the particle suspension prepared in part (a) above (1% w/v). The increase in turbidity is measured at 340 nm by the difference in absorbance 29 s and 46 s after particle addition. Table 6 shows the data for the standard curve for this assay while a comparison to a standard radioimmunoassay method is given in Table 7. (The gentamicin standards are prepared by dissolving gentamicin sulfate in normal human serum and making the appropriate dilutions.)

TABLE 6

Inhibition of Turbidimetric Activity by Serum Gentamicin

| Gentamicin Concentration (μg/mL) | Rate (mA/min at 340 nm) |
|---|---|
| 0 | 182 |
| 1 | 157 |
| 2 | 134 |
| 4 | 89 |

TABLE 6-continued

Inhibition of Turbidimetric Activity by Serum Gentamicin

| Gentamicin Concentration (μg/mL) | Rate (mA/min at 340 nm) |
|---|---|
| 8 | 47 |
| 12 | 22 |
| 16 | 14 |

TABLE 7

Comparison of Particle Gentamicin Assay to RIA

| | |
|---|---|
| Number of Samples | = 71 |
| Slope | = 1.065 |
| Y-intercept[1] | = −0.06 |
| Correlation Coefficient | = 0.985 |

[1] Y axis represents the method of this invention

EXAMPLE 11

Measurement of Tobramycin

The preparation of a tobramycin-HSA-particle reagent and the assay for tobramycin are carried out according to the procedures given for gentamicin (Example 10). Table 8 shows the inhibition of agglutination caused by serum tobramycin.

TABLE 8

Inhibition of Turbidimetric Activity by Serum Tobramycin

| Tobramycin (μg/mL) | Rate (mA/min at 340 nm) |
|---|---|
| 0 | 213 |
| 2 | 197 |
| 6 | 106 |
| 12 | 32 |
| 16 | 20 |

EXAMPLE 12

Measurement of Theophylline (a) Preparation of Theophylline-HSA Conjugate

The 8-substituted theophylline derivative necessary for coupling to the protein is synthesized by the procedure of Example 6(a).

To a solution of 25 mg of 8-(3-carboxypropyl)-1,3-dimethylxanthine (prepared in Example 6) in 1.6 mL of N,N-dimethyl formamide is added 11 mg of N-hydroxysuccinimide and 21 mg of N-ethyl-N'-(3-dimethylaminopropyl)carbodiimide hydrochloride at 0° C. The mixture is then stirred for 18 h at 4° C. and then added to a solution of human serum albumin (HSA, 120 mg) in 0.05 M bicarbonate buffer (6 mL, pH 9.0) at 0° C. The resulting mixture is maintained at pH 9.0 by the addition of 0.5 N NaOH and the mixture is stored at 4° C. for 18 h. The resulting conjugate is dialyzed against deionized water, followed by lyophilization. Analysis of the final material indicates a theophylline to HSA molar ratio of approximately 20 to 1.

(b) Preparation of Theophylline-HSA-Particle Reagent

A solution of theophylline-HSA (300 mL, 2 mg/mL) is prepared in 0.02 M bicarbonate buffer (pH 9.7). The polymer particle latex prepared in Example 1, 1.8 mL (15% solids) is then added slowly with stirring. The mixture is heated to 70° C. for 1 h followed by centrifugation (80 min, 40,000×g) to remove any unattached conjugate. The particles are resuspended in an equivalent volume of 0.1% SDS and recentrifuged.

The particle reagent is washed twice with 0.015 M phosphate buffer (ph 7.8) by centrifugation and resuspension. The final resuspension is in 0.015 M phosphate buffer (pH 7.8) containing 1 mg/mL HSA. The volume is adjusted to yield a 1% solids (w/v) particle concentration.

(c) Assay for Theophylline

The assay is performed at 37° C. on the 'aca' instrument. A 0.010 mL of sample containing theophylline is diluted with 0.030 mL of 0.15 M phosphate buffer (pH 7.8) and is added to 4.96 mL of the same phosphate buffer which also contains 2.0% (w/v) PEG 6000. 0.010 mL rabbit anti-theophylline antiserum (Kallestad Laboratories, Inc.), diluted with 0.040 mL of 0.15 M phosphate buffer containing 0.1% HSA (pH 7.8), is added and, after a 3.5-min incubation period, the reaction is initiated with 0.050 mL of the particle reagent, prepared in (b) above. The preparation of theophylline standards and the turbidity measurements are carried out as described in Example 6. Table 9 shows the data for a standard curve for the measurement of serum theophylline using the drug-conjugate-particle reagent.

TABLE 9

Inhibition of Turbidimetric Activity by Serum Theophylline

| Theophylline Concentration ($\mu$g/mL) | Rate (mA/min at 340/nm) |
| --- | --- |
| 2.5 | 224 |
| 5.0 | 208 |
| 10.0 | 158 |
| 20.0 | 86 |
| 40.0 | 46 |

EXAMPLE 13

Measurement of Thyioxine (a) Preparation of Thyroxine-Catalase Conjugate 5 g of the sodium salt of L-thyroxine (6.3 mmoles) is suspended in 20 mL 50% aqueous dioxane. 18.9 mmole (2.64 mL) triethylamine is added with stirring to the suspension followed by the addition of 1.71 g (6.93 mmoles) of N-tert-butoxycarbonyl-2-phenylacetonitrile. After stirring for 2 h at room temperature, 25 mL H$_2$O and 33 mL ethyl acetate are added and the aqueous and organic phases are separated. The aqueous phase is extracted with 33 mL ethyl acetate. Solid sodium citrate is added to the aqueous phase to lower the pH of the solution to pH 4.0. The resulting precipitate, N-(tert-butoxy)-L-thyroxine, is collected, dried under vacuum, and stored at $-20°$ C.

1.23 g (1.4 mmoles) of N-(tert-butoxy)-L-thyroxine and 0.16 g (1.4 mmoles) of N-hydroxysuccinimide are dissolved in 20 mL dimethylformamide. 0.31 g (1.5 mmoles) of dicyclohexyl carbodiimide is added to the solution which is then stirred at room temperature for 18 h. The urea precipitated during the reaction is removed by filtration and the filtrate, containing the active ester, is stored at $-20°$ C.

45 mg catalase is dissolved in 15 mL of 0.15 M sodium bicarbonate, pH 8.1. 0.30 mL of the active ester solution (150 mM) is added and the resulting suspension is stirred at 4° C. for 1 h. Any unreacted ester is removed by centrifugation at 15,000 rpm for 30 min, and the supernatant is then dialyzed against 10 mM potassium phosphate buffer, pH 7. The N-(tert-butoxy)-L-thyroxine-catalase conjugate is lyophilized and then stored at $-20°$ C.

(b) Preparation of Thyroxine-Catalase Particle Reagent 30 mg of N-(tert-butoxy)-L-thyroxine-catalase conjugate (10 mL of 3.0 mg/mL solution in 10 mM potassium phosphate buffer, pH 7) is attached to the latex polymer particles prepared according to Example 1, particle size 0.069 $\mu$m, following the procedure of Example 7 except that the reaction is performed at 40° C. in the absence of NaCl.

(c) Assay for Thyroxine

Turbidimetric assays for thyroxine are performed on the 'aca' instrument. To 4.8-mL portions of buffer containing 0.15 M phosphate buffer, pH 7.8, 2.5% (w/v) PEG 6000, 0.01% 1-anilino-8-naphthalene sulfonic acid (ANS) and 0.2% sodium salicylate are added 0.10-mL samples of thyroxine at various concentrations (prepared by dissolving the sodium salt of L-thyroxine in 0.2 M KOH and diluting into 0.15 M phosphate buffer, pH 7.8, containing 0.1% HSA). 0.050 mL of sheep anti-thyroxine antiserum (Abbott Laboratories, diluted 1/5 with phosphate buffer, pH 7, containing 0.1% HSA) is added to each portion and, after a 3.5-min incubation period at 37° C., the turbidimetric reaction is initiated by the addition of 0.050 mL of 1% thyroxine-catalase particle reagent to the 'aca' test pack. The resulting rate of increase in turbidity at 340 nm is measured after 29 s and 46 s. Table 10 shows the data for a standard curve for this assay.

TABLE 10

Inhibition of Turbidimetric Activity by Thyroxine

| Thyroxine ($\mu$g/mL) | Rate (mA/min at 340 nm) |
| --- | --- |
| 0 | 52 |
| 1 | 46 |
| 5 | 37 |
| 10 | 28 |

EXAMPLE 14

Measurement of Digoxin (a) Preparation of Digoxin-HSA Conjugate 2.40 g of digoxin is dissolved in 144 mL of absolute ethanol. 144 mL of 0.1 M sodium periodate is added dropwise with stirring and the reaction is allowed to continue for 25 min at 30° C. At this time, 3.264 mL of 0.1 M glycerol is added to stop the reaction. After 5 min, the reaction mixture is added dropwise to 3.6 g of HSA in 144 mL of deionized water (pH adjusted to 9.2 with 5% (w/v) potassium carbonate). The pH is maintained at 9.0–9.5 with 5% (w/v) potassium carbonate during the course of this reaction (30 min, 25° C.) 1.272 g of sodium borohydride is added and, after 3 h, the pH is adjusted to 6.5 with 3.65 M HCl. The solution is then dialyzed against deionized water. Following dialysis, the solution is concentrated to 130 mL with an Amicon concentrator with a PM 10 filter. The solution is then lyophilized to yield the digoxin-HSA conjugate. Analyses for digoxin content by a sulfuric acid charring procedure and for protein content by absorbance at 280 nm indicate a ratio of 13.5 digoxin molecules per protein molecule.

(b) Preparation of Digoxin-HSA Particle Reagents

The digoxin-HSA conjugate is attached to two different particle size latex polymer particles, 0.069 $\mu$m and 0.109 μm (prepared by the procedure of Example 1) by the procedure given in Example 7.

(c) Assay for Digoxin

The assays are performed at 37° C. on the 'aca' instrument. Standards (both in human serum and in a buffer containing 0.1 M glycine, 1% NaCl, 0.01% sodium azide, pH 7.5, the GBS buffer) are prepared by adding an aliquot of 1 mg/mL digoxin in DMSO and making the appropriate dilutions. 100-μl samples of the standard are added to 4.9 mL of a buffer containing 0.02 M phosphate, 0.3 M NaCl, 0.1% SDS, 0.01% sodium azide, pH 7.5 followed by the addition of 50 μl of antiserum (rabbit anti-digoxin from Cappel Laboratories, diluted 1/50 into the GBS buffer containing 1 mg/mL HSA, 1/5000 final dilution). After a 3.5-min incubation period at 37° C., 0.050 mL of each of the two different digoxin-HSA-particle reagents is added to initiate the reaction. The turbidity is measured at 340 nm either as a rate (the difference in absorbance 29 s and 46 s after initiation) or as an endpoint at various times after initiation. Table 11 shows endpoint values in milliabsorbance units obtained at 340 nm with 0.109 μm particles while Table 12 shows rate data with 0.069 μm particles. A comparison of data indicates that the time required to achieve a given mA for a 0-50 ng concentration range is reduced from 15 min to 10 min with the smaller starting particle. Table 13 shows the data for the standard curve, measuring the rate of absorbance change between 29 s and 46 s after initiation with particle reagent (based on 0.069 μm polymer particles).

In comparison, Table 14 indicates that even at a lower antibody concentration some loss in sensitivity is apparent for the particle reagents based on the larger, 0.109 μm, polymer particles. In the case of the smaller particle reagent, based on the 0.069 μm particles, at a 1/1250 antibody dilution, a 500 ng/mL sample leads to a 42% inhibition, whereas the larger particle reagent at a 1/1667 antibody dilution, leads to a 22% inhibition of the initial rate. This example illustrates an improvement in assay sensitivity for digoxin when using smaller particles.

TABLE 11

Endpoint Measurement of the Inhibition of Turbidimetric Activity by Digoxin (0.109 μm particles, antibody dilution 1/5000)

| Digoxin Concentration (ng/mL) | Endpoint (mA at 340 nm, after 15 min) |
|---|---|
| 0 | 750 |
| 50 | 700 |
| 100 | 660 |
| 250 | 620 |
| 500 | 575 |
| 1000 | 525 |

TABLE 12

Endpoint Measurement of the Inhibition of Turbidimetric Activity by Digoxin (0.069 μm particles, antibody dilution 1/5000)

| Digoxin Concentration (ng/mL) | Endpoint (mA at 340 nm) | | | |
|---|---|---|---|---|
| | 4.5 min | 10 min | 20 min | 30 min |
| 0 | 190 | 250 | 330 | 370 |
| 10 | 175 | 230 | 300 | 345 |
| 50 | 165 | 200 | 250 | 275 |
| 100 | 160 | 190 | 230 | 250 |
| 500 | 140 | 145 | 150 | 160 |

TABLE 12-continued

Endpoint Measurement of the Inhibition of Turbidimetric Activity by Digoxin (0.069 μm particles, antibody dilution 1/5000)

| Digoxin Concentration (ng/mL) | Endpoint (mA at 340 nm) | | | |
|---|---|---|---|---|
| | 4.5 min | 10 min | 20 min | 30 min |
| 1000 | 130 | 130 | 130 | 130 |

TABLE 13

Rate Measurement of the Inhibition of Turbidimetric Activity by Digoxin (antibody dilution 1/1250)

| Digoxin Concentration (ng/mL) | Rate (mA/min at 340 nm) |
|---|---|
| 0 | 81 |
| 500 | 46 |
| 1000 | 7 |
| 5000 | 0 |
| 10000 | 0 |

TABLE 14

Rate Measurement of the Inhibition of Turbidimetric Activity by Digoxin (antibody dilution 1/1667)

| Digoxin Concentration (ng/mL) | Rate (mA/min at 340 nm) |
|---|---|
| 0 | 112 |
| 125 | 105 |
| 250 | 97 |
| 500 | 87 |
| 1000 | 44 |
| 2000 | 26 |

EXAMPLE 15

Measurement of Digoxin (a) Attachment of Antibody to Polymer Particles

An immunoglobulin G fraction (IgG) of rabbit antiserum specific for digoxin-BSA conjugate (Cappel Laboratories, Inc.) is dissolved to a final IgG concentration of 1.0 mg/mL in 25 mL buffer containing 0.3 M NaCl, 0.020 M sodium phosphate and 1.0 mg/mL HSA. After adjusting the pH of the solution to 9.7 with 1 N NaOH, a 0.150-mL aliquot of the polymer particles, 14% (w/v) suspension, 0.069 m diameter, prepared in a manner similar to Example 1, is added slowly. The resulting suspension is heated to 50° C. and gently sonicated for 1 h with a Branson ® model B-22-4 water bath sonicator. Following sonication, the suspension is centrifuged for 2 h, after which the resulting pellet is resuspended in 0.1% (w/v) sodium dodecyl sulfate and centrifuged again for 40 min. The pellet from the second centrifugation is resuspended in glycine-buffered saline (GBS, 0.1 M glycine, 0.15 M NaCl, pH 7.6) and centrifuged for another 40 min. The third centrifugation step yields a pellet of IgG-polymer particle reagent (an agglutinating agent) which is resuspended in 5 mL GBS containing 1.0 mg/mL HSA and 0.1% (w/v) sodium azide. To disperse particles before use, this final suspension is sonicated for 20 min with a Heat Systems Ultrasonics ® model W-185-F sonicator. All centrifugation steps are performed with a Du Pont Sorvall ® model RC-5B centrifuge using a SM-24 rotor at 19,000 rpm.

(b) Attachment of Digoxin-HSA to Polymer Particles

A digoxin-HSA conjugate is prepared by reacting 10 mM digoxin with 50 mM sodium periodate in 50% ethanol for 30 minutes at 30° C. After adding 70 mM glycerol to stop the reaction, two volumes of this solution are added to one volume of 21.3 mg/mL HSA, adjusted to pH 10.1 with potassium carbonate. The digoxin-HSA conjugate solution is allowed to incubate for 1 h at room temperature before sodium borohydride is added to a level of 50 mM. After two additional hours, the pH is adjusted to 6.5 with 3 N HCl. The resulting conjugate solution is dialyzed against 5 mM sodium phosphate, pH 7.8.

The digoxin-HSA conjugate solution is diluted with 20 mM sodium phosphate, 0.3 M NaCl buffer (pH 9.7) to a final protein concentration of 2 mg/mL. A 0.540 mM aliquot of the polymer particle latex, 14% (w/v) suspension, 0.069 $\mu$m diameter, prepared in a manner similar to Example 1, is added to 90 mL of the conjugate solution and sonicated for 1 h at 50° C. Conditions for sonication and subsequent centrifugation are the same as given in (a) above and yield a digoxin-HSA-particle reagent.

(c) Assay for Digoxin

The assay is conducted in a Cary® 219 spectrophotometer at 37° C. with 3.0-mL quartz cuvettes containing 2.0 mL of buffer (0.150 M sodium phosphate, pH 7.8, with 4.5% (w/v) polyethylene glycol 6000). Aliquots of the (anti-digoxin) IgG-particle reagent are incubated for 5 min with this buffer and 40 $\mu$L samples containing free digoxin in GBS containing 1.0 mg/mL HSA. After incubation, aliquots of the digoxin-HSA-particle reagent are added and the initial rates of absorbance change, at 340 nm are monitored. Table 15 indicates the concentration dependence of the rates of absorbance change, while Table 16 indicates the inhibition of these rates by digoxin (40 $\mu$L of particle reagent and 50 $\mu$L of agglutinating agent).

TABLE 15

Dependence of Initial Rates Upon Particle Levels (no sample digoxin present)

| Particle Reagent ($\mu$L) | Agglutinating Agent ($\mu$L) | Initial Rate (mA/min at 340 nm) |
|---|---|---|
| 30 | 75 | 246 |
| 30 | 60 | 200 |
| 30 | 50 | 174 |
| 40 | 50 | 170 |
| 20 | 50 | 125 |
| 15 | 30 | 60 |

TABLE 16

Inhibition of Initial Rates by Digoxin

| Digoxin Concentration (ng/mL) | Initial Rate (mA/min at 340 nm) |
|---|---|
| 0 | 165 |
| 1 | 120 |
| 5 | 105 |
| 10 | 95 |
| 20 | 85 |
| 50 | 54 |
| 100 | 35 |

We claim:

1. A particle reagent having high refractive index consisting essentially of:
   (A) a polymer particle having an inner core and an outer shell wherein the inner core is a polymer having a refractive index of not less than 1.54 as measured at the wavelength of the sodium D line and wherein the outer shell is a polymer of
      (1) an ethylenically unsaturated monomer having a functional group capable of reacting with a compound of biological interest selected from the group consisting of epoxy, carboxyl, amino, hydroxyl and aldehyde,
      (2) optionally, other ethylencially unsaturated monomers in an amount sufficient to produce water insoluble polymer particles, and
      (3) not more than 10 parts by weight of the outer shell of the monomers of the inner core, said outer shell being formed by polymerization in the presence of said inner core; and
   wherein said polymer particle has an approximate diameter range of 0.03–0.1 $\mu$m and is covalently attached to
   (B) a compound of biological interest or its antibody.

2. The particle reagent of claim 1 wherein said outer shell is not more than 5 parts by weight of said polymer particle.

3. A particle reagent having high refractive index consisting essentially of:
   (A) a polymer particle having an inner core and and an outer shell wherein the inner core is a polymer having a refractive index of not less than 1.54 as measured at the wavelength of the sodium D line and wherein the outer shell is a polymer of
      (1) an ethylenically unsaturated monomer having a functional group capable of reacting with a compound of biological interest selected from the group consisting of epoxy, carboxyl, amino, hydroxyl and aldehyde,
      (2) optionally, other ethylenically unsaturated monomers in an amount sufficient to produce water insoluble polymer particles, and
      (3) not more than 10 parts by weight of the outer shell of the monomers of the inner core, said outer shell being formed by polymerizable in the presence of said inner core; and
   wherein said polymer particle has an approximate diameter range of 0.03–0.1 $\mu$m and is covalently attached to
   (B) a compound of biological interest through a proteinaceous material.

4. A method for measuring compounds of biological interest comprising the steps of
   (A) incubating
      (1) a particle reagent having high refractive index essentially of:
         (a) a polymer particle having an inner core and an outer shell wherein the inner core is a polymer having a refractive index of not less than 1.54 as measured at the wavelength of the sodium D line and wherein the outer shell is a polymer of
            (i) an ethylenically unsaturated monomer having a functional group capable of reacting with a compound of biological interest selected from the group consisting of epoxy, carboxyl, amino, hydroxyl and aldehyde,
            (ii) optionally, other ethylenically unsaturated monomers in an amount sufficient to produce water insoluble polymer particles, and
            (iii) not more than 10 parts by weight of the outer shell of the monomers of the inner core, said outer shell being formed by polymerization in the presence of said inner core and wherein said polymer particles has approximate diameter range of 0.03–0.1 μm and is covalently attached to
- (b) the compound of biological interest or its antibody;
- (2) a liquid suspected of containing the compound of biological interest; and
- (3) an agglutinating agent; and (B) photometrically measuring increased particle size resulting from agglutination.

5. The method of claim 4 wherein the polymer particle is covalently attached to the compound of biological interest.

6. The method of claim 5 wherein the agglutinating agent is selected from the group consisting of
- (A) an antibody to the compound of biological interest; and
- (B) a particle reagent having high refractive index consisting essentially of:
  - (1) a polymer particle having an inner core and an outer shell wherein the inner core is a polymer having a refractive index of not less than 1.54 as measured at the wavelength of the sodium D line and wherein the outer shell is a polymer of
    - (a) an ethylenically unsaturated monomer having a functional group capable of reaching with a compound of biological interest selected from the group consisting of epoxy, carboxyl, amino, hydroxyl and aldehyde,
    - (b) optionally, other ethylenically unsaturated monomers in an amount sufficient to produce water insoluble polymer particles, and
    - (c) not more than 10 parts by weight of the outer shell of the monomers of the inner core, said outer shell being formed by polymerization in the presence of said inner core and wherein said polymer particles has an approximate diameter range of 0.03–0.1 μm and is covalently attached to
  - (2) an antibody to the compound of biological interest.

7. The method of claim 4 wherein the polymer particle is covalently attached to an antibody of the compound of biological interest.

8. The method of claim 7 wherein the agglutinating agent is a multivalent conjugate of the compound of biological interest and a protein.

9. The method of claim 4 wherein during the incubation step (a) there is also present an agglutinating accelerator.

10. The method of claim 9 wherein the agglutinating accelerator is selected from the group consisting of polyethyene glycol and sodium dodecyl sulfate.

11. The method of claim 5 wherein the polymer particle is covalently attached to the compound of biological interest through a proteinaceous material.

12. A particle reagent having high refractive index consisting essentially of:
- (A) a polymer particle having an inner core and an outer shell wherein the inner core is a polymer having a refractive index of not less than 1.54 as measured at the wavelength of the sodium D line and wherein the outer shell is a polymer of
  - (1) an ethylenically unsaturated monomer having a functional group capable of reacting with a compound of biological interest selected from the group consisting of epoxy, carboxyl, amino, hydroxyl and aldehyde,
  - (2) optionally, other ethylenically unsaturated monomers in an amount sufficient to produce water insoluble polymer particles, and
  - (3) not more than 10 parts by weight of the outer shell of the monomers of the inner core, said outer shell being formed by polymerization in the presence of said inner core; and
wherein said polymer particle has an approximate diameter range of 0.03–0.1 μm and is covalently attached to
- (B) an antigen of the compound of biological interest.

13. The particle reagent of claim 12 wherein said outer shell is not more than 5 parts by weight of said polymer particle.

14. The particle reagent of claim 12 wherein the antigen of the compound of biological interest is attached to said polymer through a proteinaceous material.

15. A method for measuring proteins comprising the steps of
- (A) incubating
  - (1) a particle reagent having high refractive index consisting essentially of:
    - (a) a polymer particle having an inner core and an outer shell wherein the inner core is a polymer having a refractive index of not less than 1.54 as measured at the wavelength of the sodium D line and wherein the outer shell is a polymer of
      - (i) an ethylenically unsaturated monomer having a functional group capable of reacting with a compound of biological interest selected from the group consisting of epoxy, carboxyl, amino, hydroxyl and aldehyde,
      - (ii) optionally, other ethylenically unsaturated monomers in an amount sufficient to produce water insoluble polymer particles, and
      - (iii) not more than 10 parts by weight of the outer shell of the monomers of the inner core, said outer shell being formed by polymerization in the presence of said inner core and wherein said polymer particles has an approximate diameter range of 0.03–0.1 μm and is covalently attached to
    - (b) the antibody of the protein; and
  - (2) a liquid suspected of containing the compound of biological interest; and
- (B) photometrically measuring increased particle size resulting from agglutination.

* * * * *